United States Patent [19]
Botten et al.

[11] Patent Number: 6,106,507
[45] Date of Patent: Aug. 22, 2000

[54] OSTOMY APPLIANCE FACEPLATE WITH BARRIER LAYER, EXTENDED COVERING LAYER, AND UNITARY PROTECTIVE RELEASE SHEET AND METHOD OF MAKING

[75] Inventors: Ronald S. Botten, Gurnee; Walter F. Leise, Jr., Lindenhurst; John W. McDonald, Jr., Lake Zurich, all of Ill.

[73] Assignee: Hollister Incorporated, Libertyville, Ill.

[21] Appl. No.: 09/260,866

[22] Filed: Mar. 2, 1999

Related U.S. Application Data

[63] Continuation-in-part of application No. 09/095,991, Jun. 11, 1998.
[51] Int. Cl.[7] .................................................. A61F 5/44
[52] U.S. Cl. .............................. 604/338; 604/336
[58] Field of Search ............................... 604/332, 336, 604/338, 339

[56] References Cited

U.S. PATENT DOCUMENTS

| | | | |
|---|---|---|---|
| 4,419,100 | 12/1983 | Alexander | 604/339 |
| 4,710,182 | 12/1987 | Bryson | 604/339 |
| 4,775,374 | 10/1988 | Ciento et al. | 604/344 |
| 5,185,008 | 2/1993 | Lavender | 604/338 |
| 5,489,262 | 2/1996 | Cartmell et al. | 602/57 |
| 5,716,475 | 2/1998 | Botten et al. | 156/219 |

*Primary Examiner*—Wynn Wood Coggins
*Assistant Examiner*—Deborah Blyveis
*Attorney, Agent, or Firm*—Tilton Fallon Lungmus

[57] ABSTRACT

A faceplate for an ostomy appliance is disclosed in which a unitary release sheet covers both the bodyside (rear) surface of an adhesive skin barrier layer and the surrounding adhesive surface of an outwardly-projecting porous covering layer. The barrier layer is beveled to a feathered outer edge and the release sheet contacts the adhesive surface of the covering layer immediately adjacent the outer edge of said barrier layer. A continuous in-line method for making such faceplates is disclosed.

10 Claims, 2 Drawing Sheets

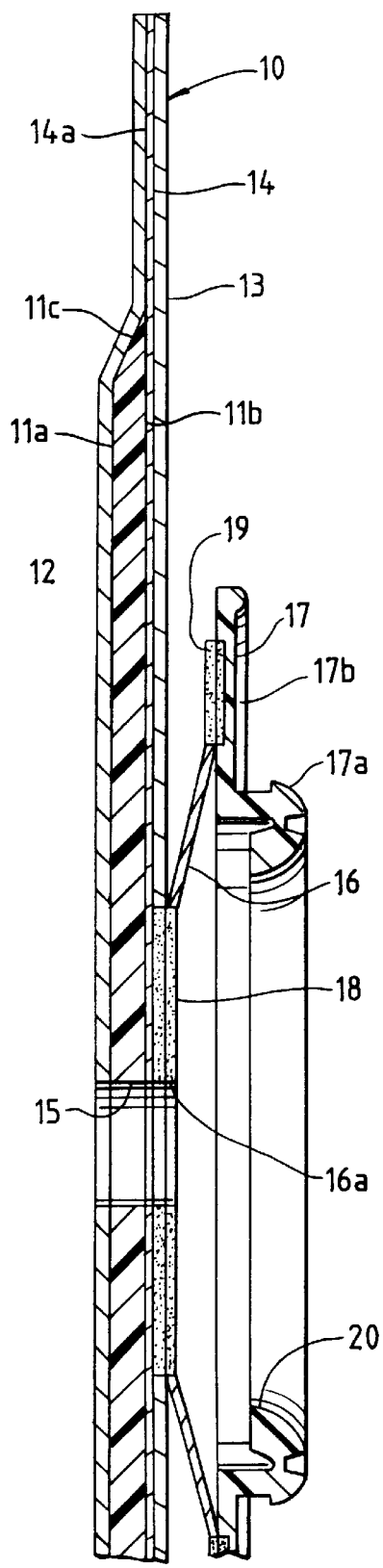
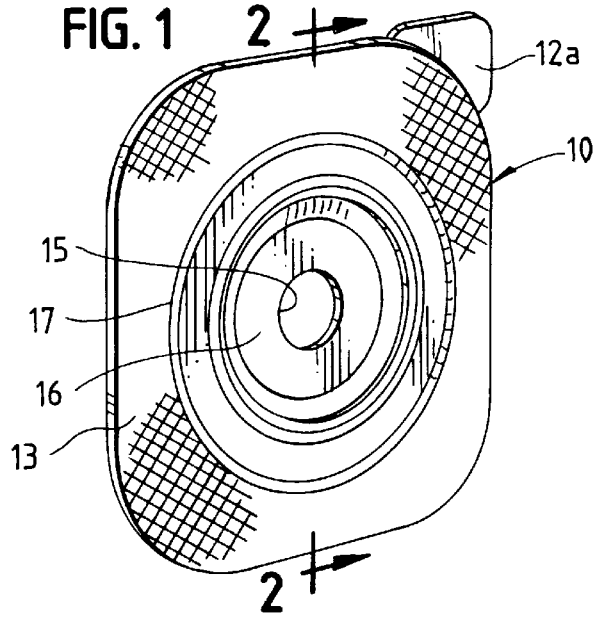
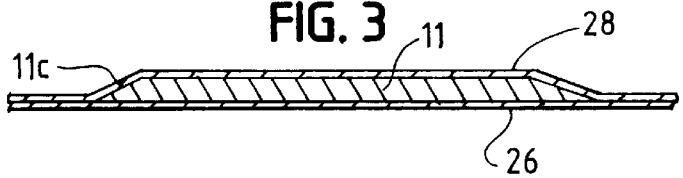
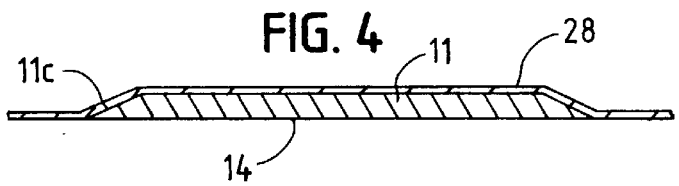
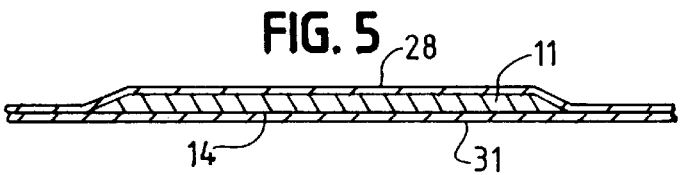
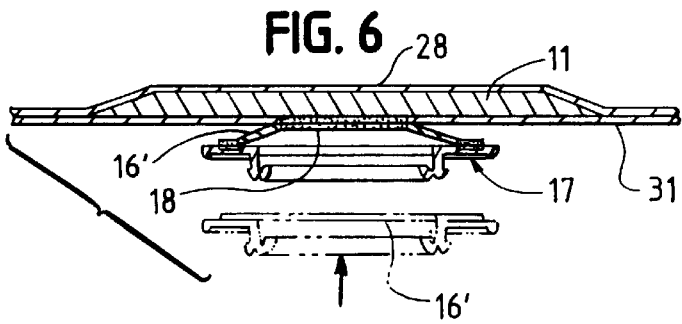

OSTOMY APPLIANCE FACEPLATE WITH BARRIER LAYER, EXTENDED COVERING LAYER, AND UNITARY PROTECTIVE RELEASE SHEET AND METHOD OF MAKING

RELATED APPLICATION

This application is a continuation-in-part of copending application Ser. No. 09/095,991 filed Jun. 11, 1998.

BACKGROUND AND SUMMARY

Alexander U.S. Pat. No. 4,419,100 discloses a two-piece ostomy appliance in which a faceplate component 12 includes a coupling ring 37 attached by thin annular web 42 to a mounting collar 30a which in turn is joined by heat seals 46 and 47 to microporous patch 30. An annular skin barrier layer 32, commonly formed of a hydrocolloid-containing moisture-absorbing and swellable adhesive material having both dry and wet tack, covers the inner portion of patch 30. To protect the bodyside surface of the skin barrier layer and the adhesive coating of that portion of the microporous patch that extends outwardly beyond the skin barrier layer, release sheets 31 and 33 separately cover each of the adhesive surfaces.

The need for providing two release sheets, one for the barrier layer and the other for the surrounding adhesive surface of the microporous patch, arises partly from cost and production considerations since the surfaces the respective release sheets cover are offset and therefore cannot easily be protected by a single release sheet and certainly not by one that is planar. While a molded release covering of developed shape has been disclosed, for example, in Bryson U.S. Pat. No. 4,710,182, such a molded covering is relatively expensive, especially since it is intended primarily to serve a protective function only until the faceplate is to be used, at which time the covering must be removed and discarded. On the other hand, providing separate protective release sheets increases the manipulative steps required by a user at the time of application and also has the disadvantage of exposing the outer edge of the skin barrier material to possible drying by exposure to air during storage prior to use. Also, if the soft, pliant barrier material has any tendency to cold flow, an arrangement utilizing two separate release sheets may be ineffective in maintaining the pliant barrier in fully covered condition prior to use.

Cartmell, et al U.S. Pat. No. 5,489,262 discloses a wound dressing having a hydrogel patch and a transparent adhesive-coated backing layer that extends outwardly beyond the outer limits of the hydrogel patch. A unitary and generally planar release sheet covers both the opposite surface of the hydrogel patch and the adhesive coating of that portion of the backing layer extending outwardly beyond the patch; however, a tenting effect results in which an annular zone of entrapped air extends about the patch and may result in undesirable drying during storage of either or both the hydrogel and the adhesive coating of the backing layer immediately surrounding the hydrogel patch.

Accordingly, a main aspect of this invention lies in providing an improved faceplate construction and its method of manufacture. A unitary release sheet protects the bodyside (rear) surfaces of a barrier layer and of an adhesive-coating covering layer that covers the opposite (front) surface of the barrier layer and projects outwardly beyond the periphery of that barrier layer. The rear surface of the barrier layer is tapered or beveled, and the contoured release sheet follows the bevel of the barrier layer and contacts the adhesive coating of the covering layer immediately adjacent the feathered outer edge of the barrier layer.

The porous covering layer is ideally formed of a soft thermoplastic fabric so that such layer may be joined by heat-sealing to a coupling ring, or to the flexible web for such a ring, or even directly to the thermoplastic film of a collection pouch. In any event, the heat seal zone extends around the stoma-receiving opening of the faceplate and seals or closes the pores of the covering layer in that zone to prevent the outward migration of fluids through the covering layer when the product is in use.

The method of this invention utilizes the injection and compression molding procedure disclosed in Botten et al U.S. Pat. No. 5,716,475 in which discrete mounds of soft, pliant barrier material are deposited one-by-one on an intermittently-advanced web, covered by a second web, and then compressed into the desired shape. In the present method, the second of such webs is the precursor for the unitary release sheet of the finished product. Following injection/compression molding of discrete mounds of barrier material between the two webs, and the replacement of the first web by a third web which is the precursor for the porous covering layer of the finished product, coupling ring elements are successively attached by heat sealing to the porous web. The final stages of the continuous in-line operation involve cutting a stoma-receiving opening through both webs as well as through the barrier material and the drumhead membrane of the coupling ring, followed by a final cutting step that defines the outer peripheral edge of the final product.

Other features, advantages and objects of the invention will become apparent from the specification and drawings.

DRAWINGS

FIG. 1 is a perspective view of an ostomy faceplate embodying this invention.

FIG. 2 is an enlarged cross sectional view taken along line 2—2 of FIG. 1.

FIGS. 3–6 are fragmentary sectional views taken in the direction of web movement and illustrating the condition of various components at different stages in the manufacturing process depicted in FIG. 7.

DETAILED DESCRIPTION OF PREFERRED EMBODIMENT

Figure 7:
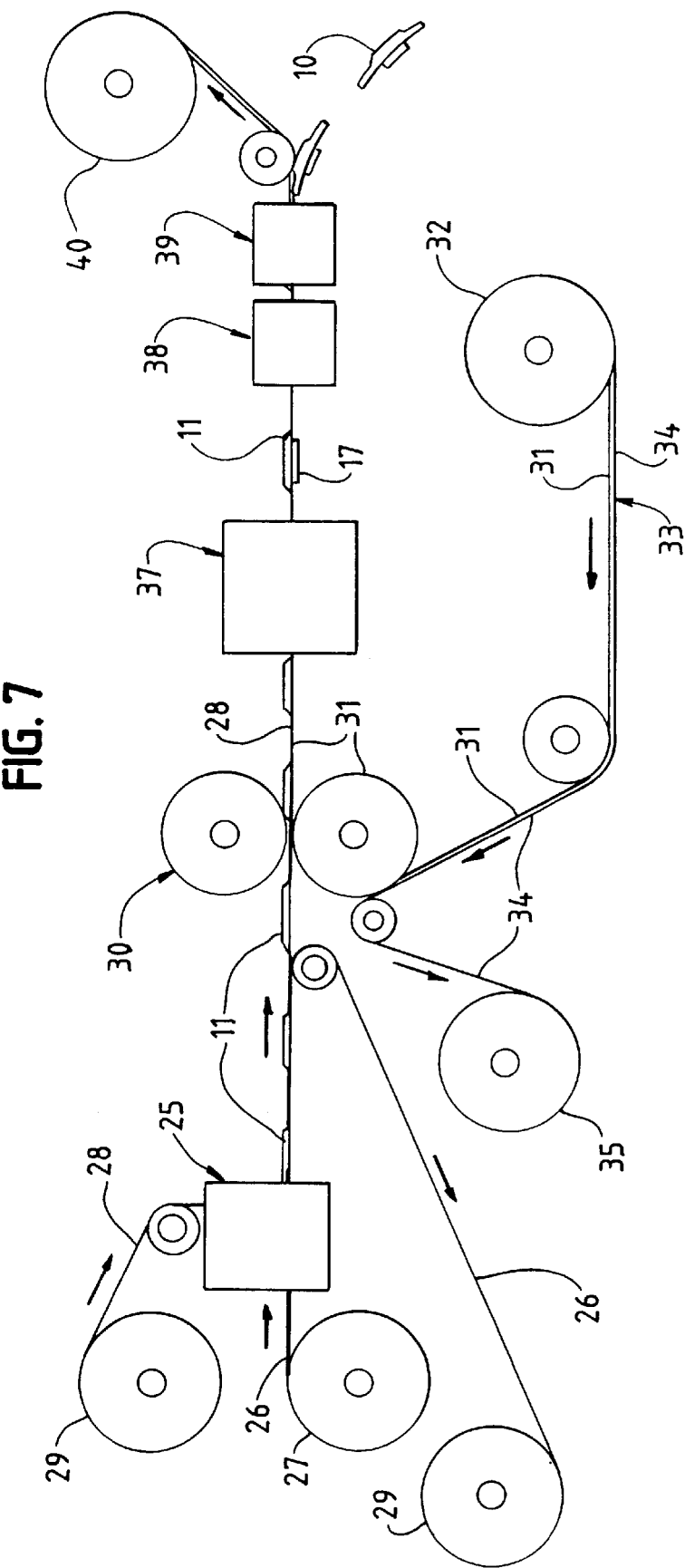
FIG. 7 is a schematic view illustrating the simultaneous procedures of the manufacturing process of this invention.

Referring to FIGS. 1 and 2, the numeral 10 generally designates a faceplate for an ostomy appliance. While the faceplate shown is for a two-piece appliance (in which a pouch component, not shown, is adapted to be mechanically coupled to and uncoupled from the faceplate component), faceplate 10 might also be part of a one-piece appliance in which a faceplate and pouch are permanently joined together. The faceplate as shown is generally rectangular (square) in outline with rounded corners, but other shapes, such as circular or oval shape, may be provided. The faceplate includes a barrier layer or wafer 11 of moisture-absorbing adhesive skin barrier material having a bodyside (rear) surface 11a covered by a removable release sheet 12 and an opposite (front) surface 11b covered by an adhesive-coated porous covering layer 13.

The term "skin barrier" is widely used in the medical field, and is so used herein, to refer to any of a variety of materials in which a soft, sticky, and pliant adhesive composition constitutes a continuous phase and particles of one or more liquid-absorbing and swellable hydrocolloids are dispersed throughout the adhesive and constitute a discontinuous phase. The adhesive phase contains at least one elastomer such as polyisobutylene, often in combination with one or more tackifiers, plasticizers, and antioxidants. An elastomer such as a styrene-isoprene-styrene block copolymer (e.g., "Cariflex" Tr-1107, from Shell Chemical Co.) or a styrene-butadiene-styrene block copolymer (e.g., "Kraton" 1100 Series, from Shell Chemical Co.) may be included, and other ABA block copolymers, such as ethylene-propylene block copolymers known as EPR rubbers have also been included in adhesive compositions for increasing the elastomeric properties of such barrier materials.

The discontinuous phase may be particles of any suitable hydrocolloid or mixtures of hydrocolloids such as sodium carboxymethylcellulose, calcium carboxymethylcellulose, pectin, gelatin, and natural gums such as guar gum, gum arabic, locust bean gum, karaya, and the like. Such hydrocolloids are water-absorbing and water-swellable. They absorb moisture from the skin and contribute to the web tack characteristics of the skin barrier material, all as well known in the art.

Surfaces 11a and 11b are generally planar and parallel, although it will be observed in FIG. 2 that the barrier layer is tapered or feathered along its outer periphery. Specifically, the rear surface 11a of the barrier layer has a gradually beveled peripheral portion 11c, with release sheet 12 following the contour of that beveled surface and then continuing outwardly beyond the outer edge of the barrier layer.

Covering layer 13 is porous (the term "porous" includes microporous), soft, flexible and heat-sealable. It may, for example, take the form of a textured thermoplastic film with a multiplicity of tiny perforations that allow for the transmission of gases, including water vapor, but resist the passage of water and other liquids. Ideally, the covering layer has at least limited stretchability so that it will readily conform to body contours, and to changes in such contours, when the faceplate is worn. A particularly effective material for such purposes is a breathable (i.e., gas-transmissible) nonwoven fabric composed of spunbonded or meltblown thermoplastic fibers. One such product is a spunbonded low density polyethylene nonwoven fabric available under the designation "Daltex" 6080-A1-UPE from Don & Low Ltd., Forfar, Scotland, but other soft, porous, heat-sealable nonwoven fabrics are available and may also be used. Flexible and resilient thermoplastic foam materials of open or semi-open cell structure are also believed suitable for fabrication of covering layer 13.

The bodyside surface of covering layer 13 is coated with a layer of pressure-sensitive adhesive 14. The adhesive layer may be formed of any suitable hypoallergenic medical-grade pressure-sensitive adhesive that is permeable to gas and water vapor. Medical-grade acrylic adhesives having such permeability or microporosity are well known and may be used here. The techniques for achieving such microporosity, which involve factors such as the rapid volatilization of solvent following a coating operation, the thinness of the coating, and the fibrous or textured character of the receiving surface are all known in the art.

Release sheet 12 is formed of any suitable material that is tough, flexible, and substantially non-stretchable. Siliconized paper may be used effectively. A polymeric material, such as polyethylene terephthalate, is particularly desirable because of its high tensile strength and transparency, but other thermoplastic materials having similar properties may be used. An anti-stick coating of silicone may be provided on the release sheet and, as shown in FIG. 1, a tab portion 12a of the release sheet projects beyond covering layer 13 to facilitate removal of the release sheet when the faceplate is to be adhered to the skin.

Of particular importance is the fact that only a single release sheet 12 is provided with that sheet covering both the planar rear surface 11a of barrier layer 11 and the pressure-sensitive adhesive coating 14a for that portion of covering layer 13 extending outwardly beyond the beveled outer edge of barrier layer 11. Since the release sheet is imperforate (except for a starter opening or stoma-receiving opening described below), it provides a unitary, unbroken but removable seal over the adhesive coating 14a and barrier layer surface 11a. Possibilities of the thin tapered outer edge of the barrier layer somehow becoming exposed or drying out during storage, as might otherwise occur if separate concentric release sheets were provided for barrier surface 11a and the surrounding pressure-sensitive adhesive surface 14a, or if the barrier were untapered and its periphery were spaced inwardly from the area of contact between release sheet 12 and the adhesive coating of covering layer 13, are thereby avoided.

A central opening 15 extends through all of the layers of the faceplate as shown in FIGS. 1 and 21. In the embodiment illustrated, opening 15 is relatively small and serves as a starter opening that may be enlarged (by cutting with scissors at the time of application) to match the size and shape of a patient's stoma. Alternatively, opening 15 may be cut to size during manufacture, with faceplates made available with openings of different sizes to meet the needs of users.

In the embodiment depicted in the drawings, the covering layer 13 of the faceplate is heat sealed to the thin flexible web 16 of a coupling ring 17. The web is circular in shape and as shown in FIG. 2, may be provided with a central opening 16a in register with opening 15. Alternatively, opening 16a may be omitted, leaving it to the user to cut (with scissors) an opening in web 16, and to enlarge opening 15 to fit the stoma, at the time of application. An annular inner portion 18 is heat sealed to covering layer 13 about openings 15 and 16a, and an outer portion 19 of the web is heat sealed to the coupling ring.

The coupling ring 17 is formed of low-density polyethylene or other flexible thermoplastic material having similar properties and has an annular connecting portion 17a defining a stoma-receiving opening 20 and a radially outwardly extending flange portion 17b for attachment to the thermoplastic film of web 16. The provision of web 16 is advantageous because it permits limited "floating" action of the coupling ring in the manner described in Alexander U.S. Pat. No. 4,419,100. A user may insert his/her fingers behind the coupling ring at the time the ring is to be joined to the mating ring of a pouch (not shown), thereby avoiding or reducing pressure against the sensitive peristomal area of the body during a coupling operation. Despite the advantages provided by such a web, however, it is to be understood that, if desired, the web may be omitted and the flange portion 17b of the coupling ring may be heat sealed or connected by other suitable means directly to covering layer 13. Also, while faceplate 10 is shown in the drawings as one component of a two-piece appliance, it may instead constitute the faceplate of a one-piece appliance with covering layer 13 being heat sealed or otherwise secured directly to the film of an ostomy pouch.

The particular coupling ring illustrated in the drawings is similar to one shown and described in Lavender U.S. Pat.

No. 5,185,008, the disclosure of which is incorporated by reference herein. It is to be understood, however, that details of the connecting portion 17a are not critical here and that a ring having a connecting portion of somewhat different construction and operation may be provided. What is significant is that, where a coupling ring is provided, its annular connecting portion 17a must extend axially away from the planar flange portion 17b, that it defines a stoma-receiving opening 20, and that it is adapted for mechanical coupling to a second ring provided by an ostomy pouch (not shown).

FIG. 7 schematically depicts a continuous in-line process for making faceplates 10. Numeral 25 designates an injection/compression molding apparatus as shown and described in Botten et al U.S. Pat. No. 5,716,475, the disclosure of which is incorporated herein by reference. The apparatus includes upper and lower platens that intermittently separate and close as a web 26 from supply roll 27 is indexed forwardly. Each time the platens separate, a discrete mound of heated skin barrier material is deposited onto web 26. A second web 28 of flexible and substantially non-stretchable material from supply roll 29 is positioned over the mound and, as the platens close together during the compression step, each mound is formed into a wafer of predetermined size and shape. This results in a series of discrete, spaced-apart wafers 11 of skin barrier material sandwiched between the first and second webs 26 and 28 and carried by such webs out of the injection/compression molding station 25 in which they were formed (FIG. 3).

It will be observed that the wafer 11 shown in FIG. 3 is identical to skin barrier layer of the finished faceplate except that the stoma-receiving opening 15 is lacking and will be formed in a later stage of the manufacturing operation. Precise control over the amount of soft skin barrier material deposited on web 26 during the injection/compression molding operation results in the formation of gradually tapered edge surfaces 11c without wastage, "tenting," or the formation of air spaces, and with sufficient barrier material to achieve a sharp peripheral edge as shown.

The upper or second web 28 is used to make the release sheets 12 of faceplates 10 and is preferably composed of a material such as polyethylene terephthalate as previously described. Lower or first web 26 may be sacrificial (as shown) or non-sacrificial. As a sacrificial element, web 26 may be formed of siliconized paper or a non-stretchable polymeric material that is coated or treated so that it may be peeled away from the wafer and rewound into roll 29. Alternatively, web 26 may take the form of a continuous belt having a non-stick support surface that travels through the injection/compression molding station 25 and extends to the delaminating/laminating station 30.

In the process as shown in FIG. 7, with web 26 being sacrificial, the wafers 11 leave the injection/compression molding station 25 in the condition shown in FIG. 3 and then, as they enter delaminating/laminating station 30, web 26 is stripped away (FIG. 4). It is immediately replaced by a fourth web 31 of flexible covering material which becomes the covering layer 13 of the finished product. As already noted, web 31 is preferably formed of nonwoven fabric that is both porous and heat-sealable. Since such nonwoven material is too soft and deformable to be processed in such an in-line operation without reinforcement, and since it is also coated with a pressure-sensitive adhesive, the web is provided by supply roll 32 in the form of a laminate 33 in which the nonwoven layer 31 is temporarily secured by the pressure-sensitive adhesive coating to a non-stretchable reinforcing release layer 34. The composite web 35 travels to the delaminating/laminating station 30 where the reinforcing backing 34 is stripped away and rewound on roll 35, and the nonwoven covering layer 31 with its adhesive coating is secured to wafers 11 and web 28 in which they are carried. Upon leaving the delaminating/laminating station the webs and wafers appear as shown in FIG. 5.

Coupling rings 17 are attached to web 31 by heat seals 18 at station 37. The coupling rings are supplied to that station with their heat-sealable webs attached but without openings 16a yet formed in such webs. Each coupling ring therefore assumes the condition depicted in broken lines in FIG. 6 with the precursor of annular web 16 taking the form of a generally planar drumhead membrane 16'. (It is to be noted, that for clarity of illustration in FIG. 2 and in the solid-line showing in FIG. 6, the heat-sealable annular web is shown slightly frusto-conical in shape, whereas at the time of attachment to web 31 at sealing station 37, the web is planar and assumes the appearance of a flat drumhead membrane.) Station 37 may consist only of a heat sealing station in which preformed coupling rings are successively attached to web 31. However, if desired, station 37 might additionally includes molding operations in which the coupling rings are formed, and in which drumhead membranes are affixed to the rings as well as subsequently attached to continuous web 31.

The combined webs 28 and 31, in the condition depicted in FIG. 6, then advance to cutting stations 38 and 39. At station 38, the central openings 15 and 16a are cut through the wafers and webs in contact with them, and in station 39 the final cutting of the outer periphery of each faceplate takes place. The faceplates 10 are discharged as finished products from station 40, and the web materials previously around such faceplates are carried as waste material to a scrap rewind roll 40.

While in the foregoing, we have disclosed embodiments of the invention in considerable detail, it will be understood by those skilled in the art that many of these details may be varied without departing from the spirit and scope of the invention.

What is claimed is:

1. An adhesive faceplate for an ostomy appliance comprising a barrier layer having first and second side surfaces and a tapered outer peripheral edge portion; said barrier layer being composed of a soft, tacky elastomer constituting a continuous first phase and liquid-absorbing hydrocolloid particles dispersed throughout constituting a discontinuous second phase; a covering layer of soft, flexible heat-sealable material having an inner portion extending along said first side surface of said barrier layer and having an integral outer portion extending outwardly beyond said peripheral edge portion of said barrier layer; a pressure-sensitive adhesive layer securing said inner portion of said covering layer to said first side surface of said barrier layer and also coating said outer portion of said covering layer; and a unitary release sheet removably covering both said second side surface of said barrier layer and said adhesive coating of said outer portion of said covering layer.

2. The faceplate of claim 1 in which said covering layer and said adhesive layer are gas and water-vapor permeable.

3. The faceplate of claims 1 or 2 in which said first surface of said barrier layer is generally planar and extends along substantially the same plane as said adhesive coating of said outer portion of said covering layer.

4. The faceplate of claim 3 in which said second surface of said barrier layer is beveled to define said tapered outer peripheral edge portion.

5. The faceplate of claim 4 in which said second surface is beveled to provide a feathered outer edge and said release sheet is contoured to match said bevel and contacts said adhesive coating of said covering layer immediately adjacent said outer edge.

6. The faceplate of claim 3 in which said release sheet is formed of transparent polymeric material.

7. The faceplate of claim 1 in which a coupling ring is heat sealed to said inner portion of said covering layer.

8. The faceplate of claim 7 in which said coupling ring includes a thin, annular web of heat-sealable material; said web having an outer periphery heat sealed to said coupling ring and an inner periphery heat sealed to said covering layer.

9. The faceplate of claim 2 in which said covering layer is a porous, nonwoven fabric formed of heat-sealable fibers.

10. The faceplate of claim 9 in which said coupling ring includes a thin, annular web of thermoplastic material; said web having an outer periphery heat sealed to said coupling ring and an inner periphery heat sealed to said covering layer; said heat seal between said inner periphery of said web and said covering layer occluding the pores of said covering layer in the area of said heat seal.

* * * * *